(12) United States Patent
Miyaki (10) Patent No.: US 9,360,550 B2
(45) Date of Patent: Jun. 7, 2016

(54) ULTRASONIC OBSERVATION APPARATUS, OPERATION METHOD OF THE SAME, AND COMPUTER READABLE RECORDING MEDIUM

(71) Applicant: OLYMPUS MEDICAL SYSTEMS CORP., Tokyo (JP)

(72) Inventor: Hironaka Miyaki, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/457,246

(22) Filed: Aug. 12, 2014

(65) Prior Publication Data
US 2015/0029821 A1    Jan. 29, 2015

Related U.S. Application Data

(63) Continuation of application No. PCT/JP2013/077249, filed on Oct. 7, 2013.

(30) Foreign Application Priority Data

Jan. 23, 2013 (JP) .................................. 2013-010539

(51) Int. Cl.
*G01S 7/52* (2006.01)
*A61B 8/08* (2006.01)
(Continued)

(52) U.S. Cl.
CPC ........... *G01S 7/52017* (2013.01); *A61B 8/5207* (2013.01); *G01S 7/52033* (2013.01); *G01S 7/52036* (2013.01); *G01S 15/02* (2013.01); *A61B 8/14* (2013.01); *A61B 8/5269* (2013.01)

(58) Field of Classification Search
CPC ....... G01S 7/52; G01S 15/02; G01S 7/52036; G01S 7/52033; G01S 7/52017; A61B 8/08; A61B 8/14; A61B 8/5207

USPC .......................................................... 367/11
See application file for complete search history.

(56) References Cited

U.S. PATENT DOCUMENTS 5,911,160 A    6/1999 Abe et al.
7,473,225 B2 *   1/2009 Azuma et al. ................. 600/442
(Continued)

FOREIGN PATENT DOCUMENTS

CN    102958447 A    3/2013
JP    08-131435 A    5/1996
(Continued)

OTHER PUBLICATIONS

Cloostermans, A beam corrected estimation of the frequency dependent attenuation of biological tissues from backscattered ultrasound, Ultrasonic Imaging 5,136-147 (1983).*
(Continued)

*Primary Examiner* — Luke Ratcliffe
*Assistant Examiner* — Amienatta M Ndure Jobe
(74) *Attorney, Agent, or Firm* — Scully, Scott, Murphy & Presser, P.C.

(57) ABSTRACT

An ultrasonic observation apparatus includes: a first conversion unit that converts an ultrasonic signal as a time domain signal reflected from a specimen into a frequency domain signal; a regression analysis unit that calculates a regression expression for the frequency domain signal; an attenuation correction coefficient calculation unit that calculates an attenuation correction coefficient which is obtained by dividing a difference between first-order coefficients in the regression expressions at two points having different reception depths by a difference between the reception depths at the two points; an attenuation correction processing unit that performs attenuation correction processing on the frequency domain signal based on the attenuation correction coefficient; a second conversion unit that converts the frequency domain signal after the attenuation correction processing, into a second time domain signal; and an image data generation unit that generates ultrasonic image data based on the second time domain signal.

6 Claims, 9 Drawing Sheets

(51) Int. Cl.
*G01S 15/02* (2006.01)
*A61B 8/14* (2006.01)

(56) References Cited

U.S. PATENT DOCUMENTS

| | | | |
|---|---|---|---|
| 7,691,064 B2* | 4/2010 | Cerofolini | 600/458 |
| 7,740,583 B2* | 6/2010 | Rigby et al. | 600/437 |
| 8,047,994 B2* | 11/2011 | Cerofolini | 600/458 |
| 8,444,563 B2* | 5/2013 | Imamura et al. | 600/443 |
| 8,480,586 B2* | 7/2013 | Tsao et al. | 600/443 |
| 8,619,142 B2* | 12/2013 | Miyaki | 348/163 |
| 8,917,919 B2* | 12/2014 | Noguchi | 382/128 |
| 2001/0016685 A1* | 8/2001 | Tsao et al. | 600/437 |
| 2002/0002333 A1* | 1/2002 | Angelsen et al. | 600/443 |
| 2004/0039286 A1* | 2/2004 | Kuban et al. | 600/467 |
| 2004/0122326 A1* | 6/2004 | Nair et al. | 600/467 |
| 2004/0152983 A1* | 8/2004 | Vince et al. | 600/454 |
| 2005/0203405 A1* | 9/2005 | Tsujita | 600/455 |
| 2006/0052702 A1 | 3/2006 | Matsumura et al. | |
| 2007/0160275 A1* | 7/2007 | Sathyanarayana | 382/128 |
| 2007/0239007 A1* | 10/2007 | Silverman et al. | 600/437 |
| 2008/0051659 A1* | 2/2008 | Waki et al. | 600/443 |
| 2008/0287795 A1* | 11/2008 | Klingensmith et al. | 600/443 |
| 2012/0310087 A1 | 12/2012 | Miyaki et al. | |
| 2013/0030296 A1 | 1/2013 | Miyaki | |
| 2013/0113938 A1 | 5/2013 | Miyaki | |

FOREIGN PATENT DOCUMENTS

| | | |
|---|---|---|
| JP | 09-173334 A | 7/1997 |
| JP | 10-033529 A | 2/1998 |
| JP | 2004-113364 A | 4/2004 |
| JP | 2004-135929 A | 5/2004 |
| JP | 2005-152675 A | 6/2005 |
| WO | WO 2012/063929 A1 | 5/2012 |
| WO | WO 2012/063976 A1 | 5/2012 |
| WO | WO 2012/133878 A1 | 10/2012 |

OTHER PUBLICATIONS

Decision of a Patent Grant dated Oct. 14, 2014 from related Japanese Patent Application No. 2014-537398, together with an English language translation.

International Search Report dated Nov. 5, 2013 issued in PCT/JP2013/077249.

Claesson, I., et al, "Frequency- and Depth-Dependent Compensation of Ultrasonic Signals", IEEE Transactions on Ultrasonics, Ferroelectronics, and Frequency Control, Sep. 1988, pp. 582-592, vol. 35. No. 5.

* cited by examiner

ULTRASONIC OBSERVATION APPARATUS, OPERATION METHOD OF THE SAME, AND COMPUTER READABLE RECORDING MEDIUM

CROSS REFERENCES TO RELATED APPLICATIONS

This application is a continuation of PCT international application Ser. No. PCT/JP2013/077249 filed on Oct. 7, 2013 which designates the United States, incorporated herein by reference, and which claims the benefit of priority from Japanese Patent Application No. 2013-010539, filed on Jan. 23, 2013, incorporated herein by reference.

BACKGROUND OF THE INVENTION

1. Field of the Invention

The present invention relates to an ultrasonic observation apparatus for observing tissues of a specimen using ultrasonic waves, an operation method of the ultrasonic observation apparatus, and a computer readable recording medium.

2. Description of the Related Art

As an examination technique for breast cancer and the like using ultrasonic waves, a technique called ultrasonic elastography has been known (for example, see Japanese Laid-open Patent Publication No. 2004-135929). Ultrasonic elastography is a technique utilizing the fact that stiffness of cancer or a tumor tissue inside a living body differs depending on the progress state of a disease and each living body. In this technique, in a state where an examined portion is pressed from the outside, a quantity of distortion and a degree of elasticity of the examined portion are measured using ultrasonic waves, and the measurement result is displayed in an image as a tomographic image.

As an ultrasonic wave is attenuated in a living body, it is important to know the quantity of attenuation or the attenuation correction coefficient when an examination is conducted. As a technique of correcting attenuation caused by propagation of an ultrasonic wave, STC (Sensitivity Time Control) correction which changes an amplification factor according to a propagation distance has been known (for example, see Japanese Laid-open Patent Publication No. 8-131435). This technique is to change the amplification factor of a signal according to a reception depth, and is not able to correct attenuation depending on a frequency. For this reason, in an area having a large reception depth and distant from the ultrasonic transducer, a high-frequency component is attenuated and the spatial resolution is reduced.

Meanwhile, a technique for performing correction depending on the frequency of a signal is also known (for example, see Japanese Laid-open Patent Publication No. 9-173334). In this technique, after performing fast Fourier transform (FFT) on a received signal, attenuation correction is performed so as to conform with a given frequency spectrum, and then inverse fast Fourier transform (IFFT) is performed.

Further, there is also a technique in which, with respect to a signal on which FFT has been performed, an inverse number is obtained for each frequency, and a spectrum, which increases or decreases in an inverse pattern of that of a measurement signal, is obtained as a spectrum of a correction coefficient, and after multiplying the correction coefficient with the measured frequency spectrum of the signal, IFFT is performed (for example, see Japanese Laid-open Patent Publication No. 10-33529).

SUMMARY OF THE INVENTION

An ultrasonic observation apparatus according to one aspect of the invention includes: a transmitting and receiving unit configured to transmit an ultrasonic signal, which is a time domain signal, to a specimen, and receive the ultrasonic signal reflected from the specimen; a first conversion unit configured to convert the ultrasonic signal received by the transmitting and receiving unit into a frequency domain signal; a regression analysis unit configured to calculate a regression expression for the frequency domain signal converted by the first conversion unit; an attenuation correction coefficient calculation unit configured to calculate an attenuation correction coefficient which is obtained by dividing a difference between first-order coefficients in the regression expressions at two points having different reception depths by a difference between the reception depths at the two points; an attenuation correction processing unit configured to perform attenuation correction processing on the frequency domain signal based on the attenuation correction coefficient calculated by the attenuation correction coefficient calculation unit; a second conversion unit configured to convert the frequency domain signal, on which the attenuation correction processing has been performed by the attenuation correction processing unit, into a second time domain signal; and an image data generation unit configured to generate ultrasonic image data based on the second time domain signal.

An operation method of an ultrasonic observation apparatus according to another aspect of the invention is an operation method of an ultrasonic observation apparatus that transmits an ultrasonic signal, which is a time domain signal, to a specimen and receives the ultrasonic signal reflected from the specimen. The method includes: converting the received ultrasonic signal into a frequency domain signal by a first conversion unit; calculating a regression expression for the frequency domain signal by a regression analysis unit; calculating an attenuation correction coefficient by an attenuation correction coefficient calculation unit, the attenuation correction coefficient being obtained by dividing a difference between first-order coefficients in the regression expressions at two points having different reception depths by a difference between the reception depths at the two points; performing attenuation correction processing on the frequency domain signal based on the attenuation correction coefficient, using an attenuation correction processing unit; converting the frequency domain signal, on which the attenuation correction processing has been performed, into a second time domain signal, using a second conversion unit; and generating ultrasonic image data based on the second time domain signal, using an image data generation unit.

A non-transitory computer readable recording medium according to still another aspect of the invention is a non-transitory computer readable recording medium with an executable program stored thereon. The program instructs a processor to perform: converting the received ultrasonic signal into a frequency domain signal by a first conversion unit; calculating a regression expression for the frequency domain signal by a regression analysis unit; calculating an attenuation correction coefficient by an attenuation correction coefficient calculation unit, the attenuation correction coefficient being obtained by dividing a difference between first-order coefficients in the regression expressions at two points having different reception depths by a difference between the reception depths at the two points; performing attenuation correction processing on the frequency domain signal based on the attenuation correction coefficient, using an attenuation correction processing unit; converting the frequency domain signal, on which the attenuation correction processing has been performed, into a second time domain signal, using a second conversion unit; and generating ultrasonic image data based on the second time domain signal, using an image data generation unit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, modes for carrying out the present invention (hereinafter referred to as "embodiments") will be described with reference to the accompanying drawings.

First Embodiment

Figure 1:
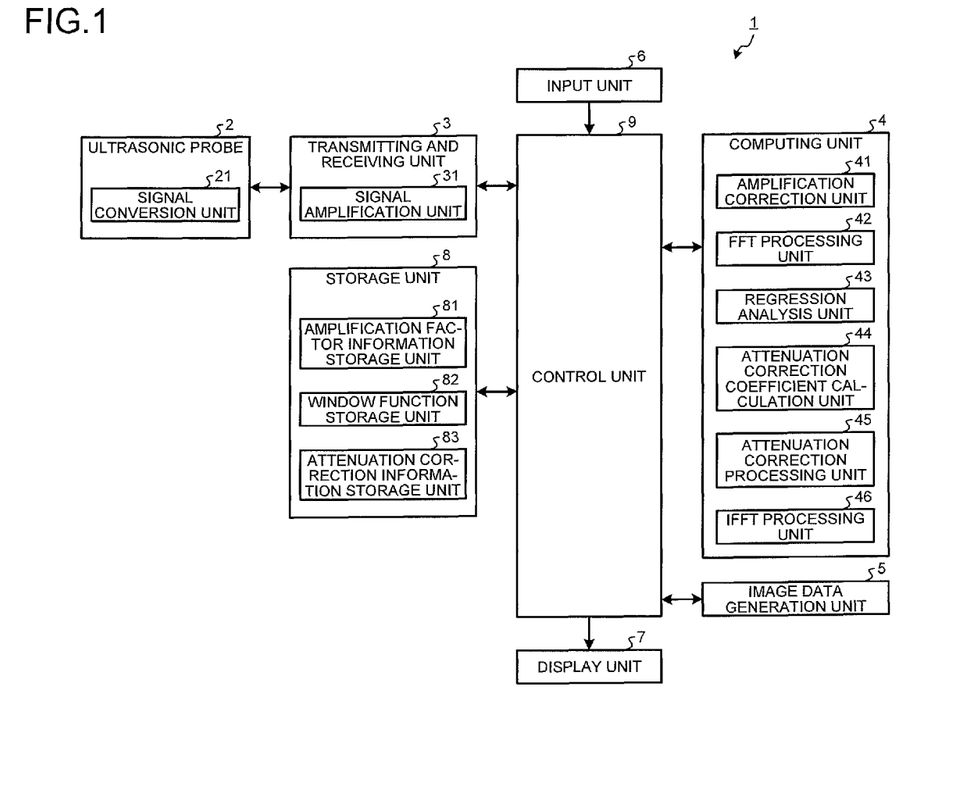
FIG. 1 is a block diagram illustrating a configuration of an ultrasonic observation apparatus according to a first embodiment of the present invention.

FIG. 1 is a block diagram illustrating a configuration of an ultrasonic observation apparatus according to a first embodiment of the present invention. An ultrasonic observation apparatus 1 illustrated in the drawing is an apparatus for observing a specimen to be diagnosed using ultrasonic waves.

The ultrasonic observation apparatus 1 includes an ultrasonic probe 2 which outputs ultrasonic pulses to the outside and receives ultrasonic echoes reflected outside, a transmitting and receiving unit 3 which transmits and receives electrical signals to/from the ultrasonic probe 2, a computing unit 4 which performs arithmetic operation on electrical echo signals obtained by converting ultrasonic echoes, an image data generation unit 5 which generates image data corresponding to electrical echo signals obtained by converting ultrasonic echoes, an input unit 6 which is realized using interfaces such as a keyboard, a mouse, a touch panel, and the like, and accepts inputs of various types of information, a display unit 7 which is realized by a display panel formed of liquid crystal, organic EL, or the like, and displays various types of information including images generated by the image data generation unit 5, a storage unit 8 which stores various types of information including window functions to be used for frequency analysis, and a control unit 9 which controls operation of the ultrasonic observation apparatus 1.

The ultrasonic probe 2 includes a signal conversion unit 21 which converts an electrical pulse signal received from the transmitting and receiving unit 3 into an ultrasonic pulse (acoustic pulse signal), and converts an ultrasonic echo reflected on an outside specimen into an electrical echo signal. The ultrasonic probe 2 may be a probe which allows an ultrasonic transducer to perform scanning mechanically, or a probe which allows a plurality of ultrasonic transducers to perform scanning electronically.

The transmitting and receiving unit 3 is electrically connected to the ultrasonic probe 2, and transmits pulse signals to the ultrasonic probe 2 and receives echo signals, which are reception signals, from the ultrasonic probe 2. Specifically, the transmitting and receiving unit 3 generates pulse signals based on a preset waveform and transmission timing, and transmits the generated pulse signals to the ultrasonic probe 2.

Figure 2:
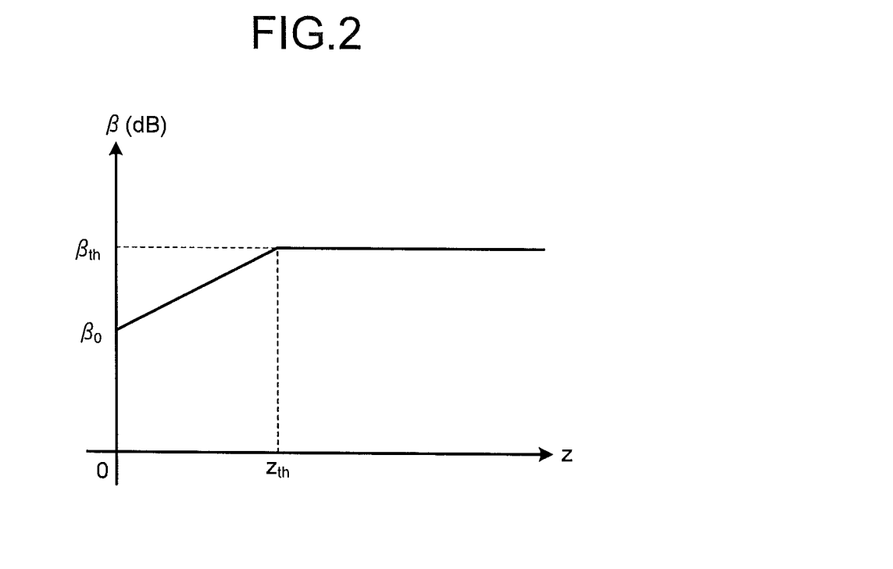
FIG. 2 is a diagram illustrating a relationship between a reception depth and an amplification factor of an echo signal in amplification processing performed by a signal amplification unit of the ultrasonic observation apparatus according to the first embodiment of the present invention.

The transmitting and receiving unit 3 includes a signal amplification unit 31 which amplifies echo signals. Specifically, the signal amplification unit 31 performs STC correction in which an echo signal having a larger reception depth is amplified with a higher amplification factor. FIG. 2 is a diagram illustrating a relationship between the reception depth of an echo signal and the amplification factor. A reception depth z illustrated in FIG. 2 is a quantity calculated based on an elapsed period of time from the point of time when reception of an ultrasonic wave begins. As illustrated in FIG. 2, if the reception depth z is smaller than a threshold $z_{th}$, an amplification factor $\beta$ (dB) increases linearly from $\beta_0$ to $\beta_{th}$ ($>\beta_0$) with an increase in the reception depth z. Further, if the reception depth z is equal to or larger than the threshold $z_{th}$, the amplification factor $\beta$ takes a constant value $\beta_{th}$. The value of the threshold $z_{th}$ is a value at which an ultrasonic signal received from a specimen is attenuated almost completely so that noise becomes dominant. More generally, if the reception depth z is smaller than the threshold $z_{th}$, it is only necessary that the amplification factor $\beta$ increases monotonically with an increase in the reception depth z.

The transmitting and receiving unit 3 performs processing such as filtering and the like on an echo signal amplified by the signal amplification unit 31, and then performs A/D conversion to thereby generate and output a digital RF signal of a time domain. It is noted that, in the case where the ultrasonic probe 2 is a probe which allows a plurality of ultrasonic transducers to perform scanning electronically, the transmitting and receiving unit 3 includes a multi-channel circuit for beam synthesis corresponding to the ultrasonic transducers.

The computing unit 4 includes an amplification correction unit 41 which performs amplification correction for making the amplification factor constant, independent of the reception depth, on a digital RF signal output from the transmitting and receiving unit 3, an FFT processing unit 42 which performs fast Fourier transform (FFT) on the digital RF signal, on which amplification correction has been performed, to thereby obtain a signal of a frequency domain (frequency spectrum), a regression analysis unit 43 which performs regression analysis on the signal on which FFT has been performed by the FFT processing unit 42, an attenuation correction coefficient calculation unit 44 which calculates an attenuation correction coefficient based on the result of regression analysis performed by the regression analysis unit 43, an attenuation correction processing unit 45 which performs attenuation correction of the signal, on which FFT has been performed, using the attenuation correction coefficient calculated by the attenuation correction coefficient calculation unit 44, and an IFFT processing unit 46 which performs inverse fast Fourier transform (IFFT) on the signal, on which attenuation correction has been performed by the attenuation correction processing unit 45, to thereby obtain a signal of a time domain.

Figure 3:
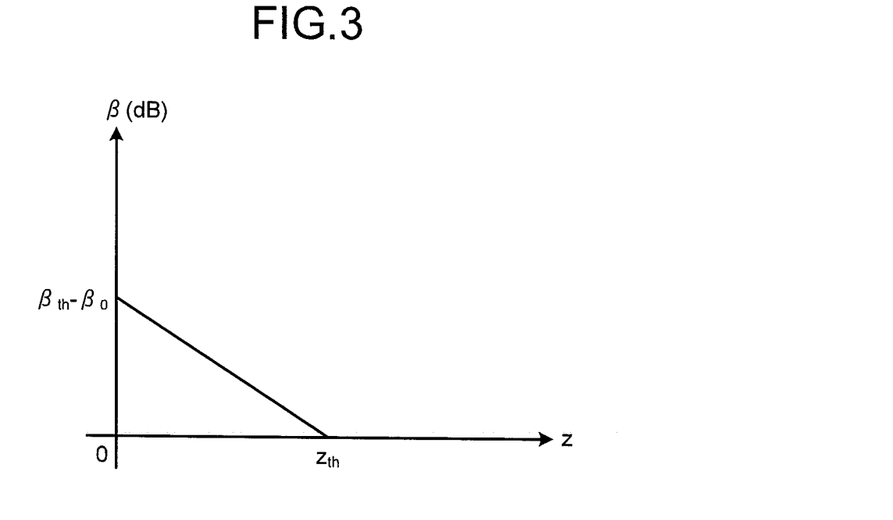
FIG. 3 is a diagram illustrating a relationship between a reception depth and an amplification factor in amplification processing performed by an amplification correction unit of the ultrasonic observation apparatus according to the first embodiment of the present invention.

FIG. 3 is a diagram illustrating a relationship between the reception depth and the amplification factor in amplification processing performed by the amplification correction unit 41. As illustrated in FIG. 3, the amplification factor β (dB) in the amplification processing performed by the amplification correction unit 41 takes a maximum value $\beta_{th}-\beta_0$ when the reception depth z is zero, decreases linearly until the reception depth z reaches the threshold $z_{th}$ from zero, and takes zero when the reception depth z is equal to or larger than the threshold $z_{th}$. By performing amplification correction on a digital RF signal by the amplification correction unit 41 using the amplification factor determined in this way, an effect of STC correction by the signal amplification unit 31 is offset, whereby a signal having a constant amplification factor $\beta_{th}$ can be output. It is noted that the relationship between the reception depth z and the amplification factor β in the amplification processing performed by the amplification correction unit 41 varies depending on the relationship between the reception depth and the amplification factor in the signal amplification unit 31, of course.

The FFT processing unit 42 calculates a signal of a frequency domain, that is, a frequency spectrum, by performing FFT on an FFT data group including a given amount of data, with respect to each acoustic ray (line data) to be processed. The FFT processing unit 42 corresponds to a first conversion unit which converts an ultrasonic signal received by the transmitting and receiving unit 3 into a frequency domain signal. The calculation result of FFT is obtained as a complex number, and is stored in the storage unit 8. A frequency spectrum shows a different tendency depending on the tissue characterization of a specimen. This is because a frequency spectrum is correlated with the size, density, acoustic impedance, and the like of the specimen as a scatterer which scatters ultrasonic waves.

The regression analysis unit 43 performs regression analysis on each spectrum having an intensity I(f), where the frequency spectrum of the reception depths z at two or more points (distances from the ultrasonic transducer provided to the ultrasonic probe 2) calculated by the FFT processing unit 42 is represented by the intensity I(f,z) and the phase φ(f,z) ("f" represents a frequency), to thereby calculates a regression expression which is a linear expression. The first-order coefficient of the regression expression (hereinafter referred to as "slope") is correlated with the size of the attenuation correction coefficient of an ultrasonic wave. Accordingly, as the attenuation correction coefficient is larger, a change of the slope with respect to a propagation distance of the ultrasonic wave becomes larger.

The attenuation correction coefficient calculation unit 44 calculates an attenuation correction coefficient of an ultrasonic wave using the slopes of the regression expressions extracted by the regression analysis unit 43, and the reception depths at two or more points with which the regression expressions are calculated. Specifically, assuming that the slope of the regression expression of the frequency spectrum at a reception depth $z_1$ is $a_1$ and the slope of the regression expression of the frequency spectrum at a reception depth $z_2$ is $a_2$, the attenuation correction coefficient calculation unit 44 calculates an attenuation correction coefficient α between the two points $z_1$ and $z_2$ ($>z_1$) from the following expression (1):

$$\alpha = (a_1 - a_2)/(z_2 - z_1) \quad (1)$$

As obvious from Expression (1), the attenuation correction coefficient α corresponds to an average attenuation correction coefficient between the two points. Here, the reception depths $z_1$ and $z_2$ in Expression (1) can be calculated based on the reception times of echo signals. It is noted that a difference $z_2-z_1$ between the reception depths of the two points is preferably almost similar to the wavelength of the ultrasonic wave (approximately several mm, for example) output by the ultrasonic probe 2.

The attenuation correction processing unit 45 performs attenuation correction processing of the frequency spectrum based on the attenuation correction coefficient calculated by the attenuation correction coefficient calculation unit 44. Specifically, the attenuation correction processing unit 45 corrects the intensity $I(f,z_1)$ excluding the phase component of the frequency spectrum of the reception depth $z_1$ as follows:

$$I'(f,z_1) = I(f,z_1) + 2\alpha(z_1)z_1 f \quad (2)$$

Here, $\alpha(z_1)$ in right-hand side is given by α of Expression (1), for example.

The IFFT processing unit 46 performs IFFT processing on the frequency spectrum corrected by the attenuation correction processing unit 45 to thereby obtain a signal of a time domain (second time domain signal). The IFFT processing unit 46 corresponds to a second conversion unit which converts the frequency domain signal, on which attenuation correction has been performed by the attenuation correction processing unit 45, into a second time domain signal. The second time domain signal is an ultrasonic signal on which attenuation correction has been performed corresponding to the reception depth and the frequency. Accordingly, it is possible to obtain an ultrasonic signal in which a high-frequency component is also restored, which is different from the processing which only increases the amplification factor of a signal as in the conventional art.

The image data generation unit 5 performs signal processing on the real part of the second time domain signal, on which attenuation correction has been performed by the computing unit 4, using well-known art such as filter processing, logarithmic compression, gain processing, contrast processing, and the like. The image data generation unit 5 also performs decimation of data and the like corresponding to the data step width determined depending on the image display range in the display unit 7, to thereby generate ultrasonic image data. The ultrasonic image data corresponds to data on which attenuation correction depending on the frequency is performed on B mode image data which is a grayscale image, in which the values of R (red), G (green), and B (blue) being variables when an RGB color system is adopted as a color space are conformed.

The storage unit 8 includes an amplification factor information storage unit 81 which stores information of amplification factors to be referred to when the signal amplification unit 31 and the amplification correction unit 41 perform amplification processing, a window function storage unit 82 which stores at least one of window functions such as Hamming, Hanning, and Blackman as a window function to be used in FFT processing performed by the FFT processing unit 42, and an attenuation correction information storage unit 83 which stores the attenuation correction coefficient α calculated by the attenuation correction coefficient calculation unit 44, along with the slopes $a_1$ and $a_2$ and the reception depths $z_1$ and $z_2$ in Expression (1).

The storage unit 8 is realized using a ROM in which an operation program of the ultrasonic observation apparatus according to the first embodiment, a program for activating a specified OS, and the like have been stored in advance, a RAM in which operation parameters of various types of processing, data, and the like are stored, and the like.

The control unit 9 is realized using a CPU and the like, and collectively controls operation of the ultrasonic observation apparatus 1. The control unit 9 reads, from the storage unit 8, information and various types of programs including the operation program of the ultrasonic observation apparatus described above stored in the storage unit 8, to thereby perform arithmetic processing related to an operation method of the ultrasonic observation apparatus according to the first embodiment.

It is noted that the operation program of the ultrasonic observation apparatus according to the first embodiment may be recorded on a computer readable recording medium such as a hard disk, a flash memory, a CD-ROM, a DVD-ROM, or a flexible disk so as to be made available widely.

Figure 4:
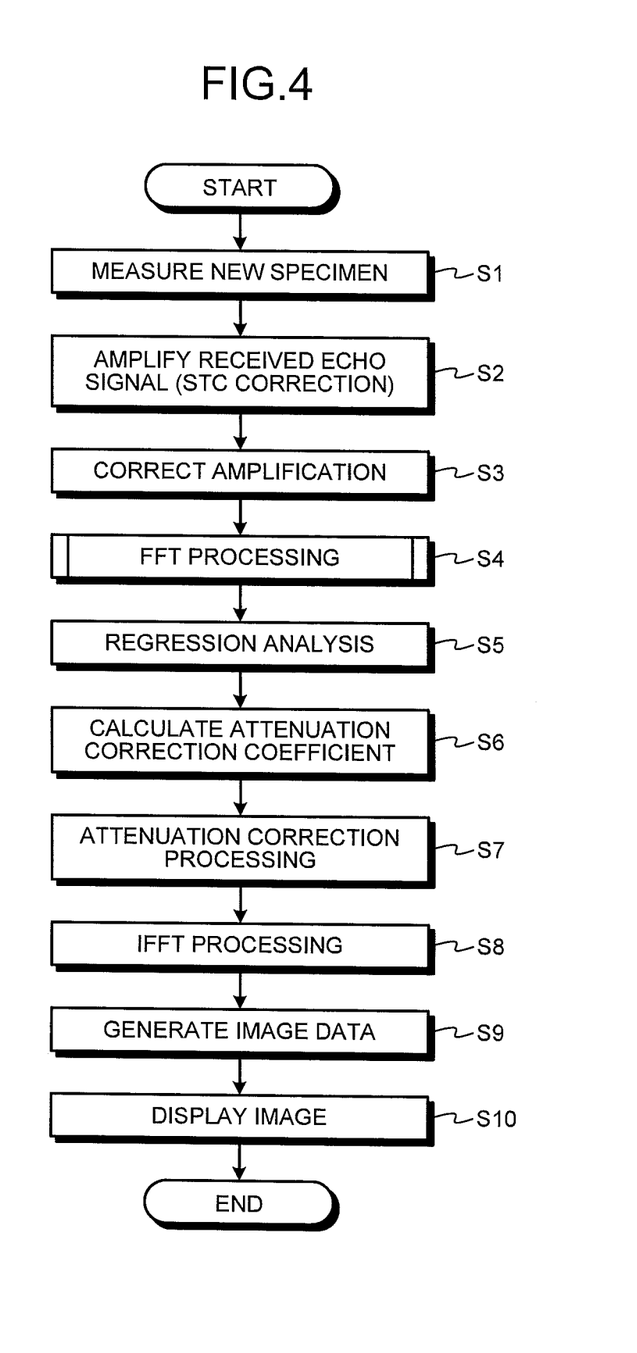
FIG. 4 is a flowchart illustrating the outline of processing performed by the ultrasonic observation apparatus according to the first embodiment of the present invention.

FIG. 4 is a flowchart illustrating the outline of processing by the ultrasonic observation apparatus 1 having the configuration described above. In FIG. 4, the ultrasonic observation apparatus 1 first measures a new specimen by the ultrasonic probe 2 (step S1).

Subsequently, the signal amplification unit 31 which has received an echo signal from the ultrasonic probe 2 amplifies the echo signal (step S2). At this step, the signal amplification unit 31 performs amplification (STC correction) based on the relationship between the amplification factor and the reception depth illustrated in FIG. 2.

Then, the amplification correction unit 41 performs correction on the signal output from the transmitting and receiving unit 3 so as to make the amplification factor constant independent of the reception depth (step S3). At this step, the amplification correction unit 41 performs amplification correction based on the relationship between the amplification factor and the reception depth illustrated in FIG. 3, for example.

Figure 5:
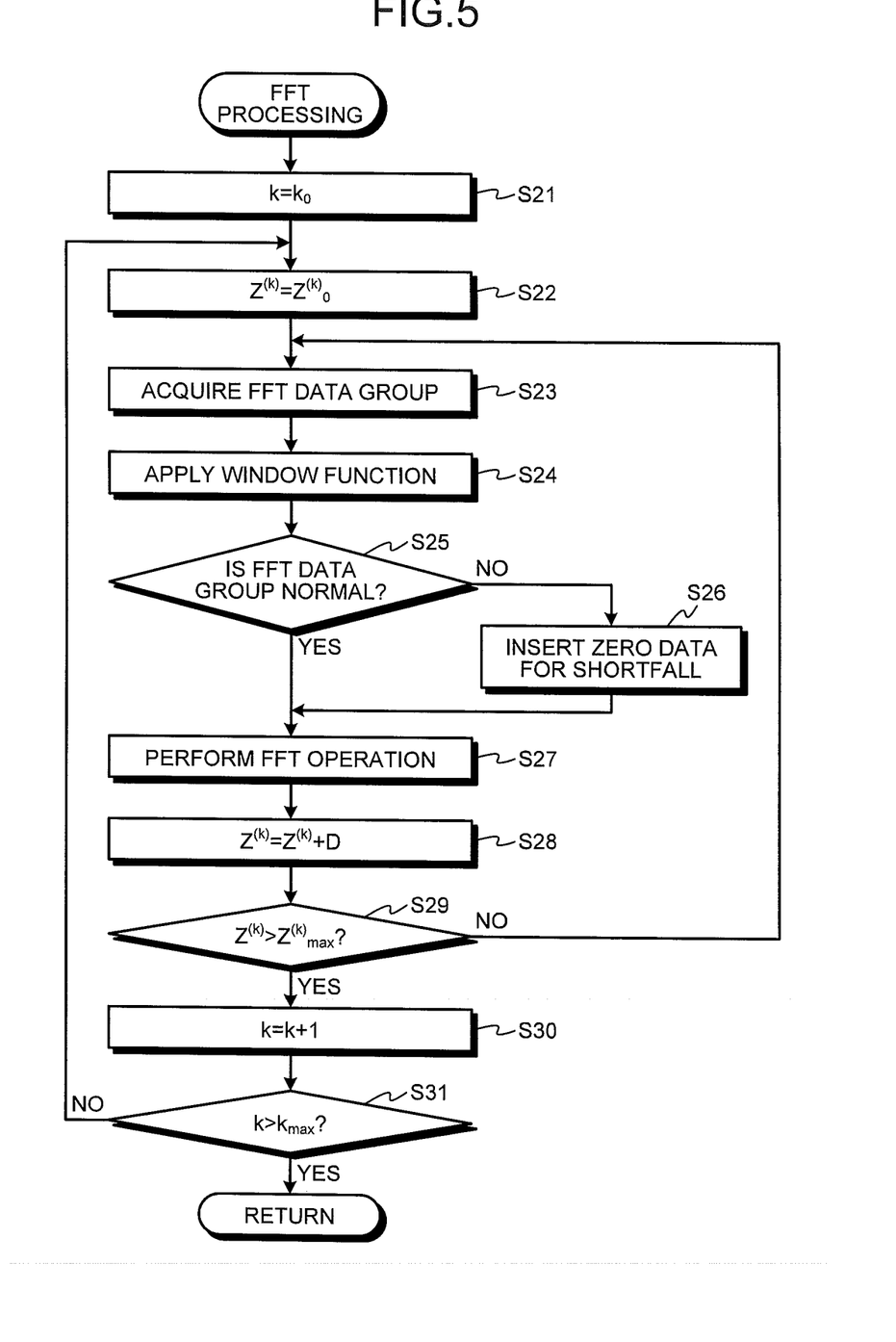
FIG. 5 is a flowchart illustrating the outline of FFT processing performed by an FFT processing unit of the ultrasonic observation apparatus according to the first embodiment of the present invention.

Subsequently, the FFT processing unit 42 performs FFT processing on the signal on which amplification correction has been performed (step S4). FIG. 5 is a flowchart illustrating the outline of the FFT processing performed by the FFT processing unit 42. Hereinafter, the FFT processing performed by the FFT processing unit 42 will be described in detail with reference to FIG. 5.

First, the FFT processing unit 42 sets a counter k, for identifying an acoustic ray to be analyzed, to be $k_0$ (step S21).

Figure 6:
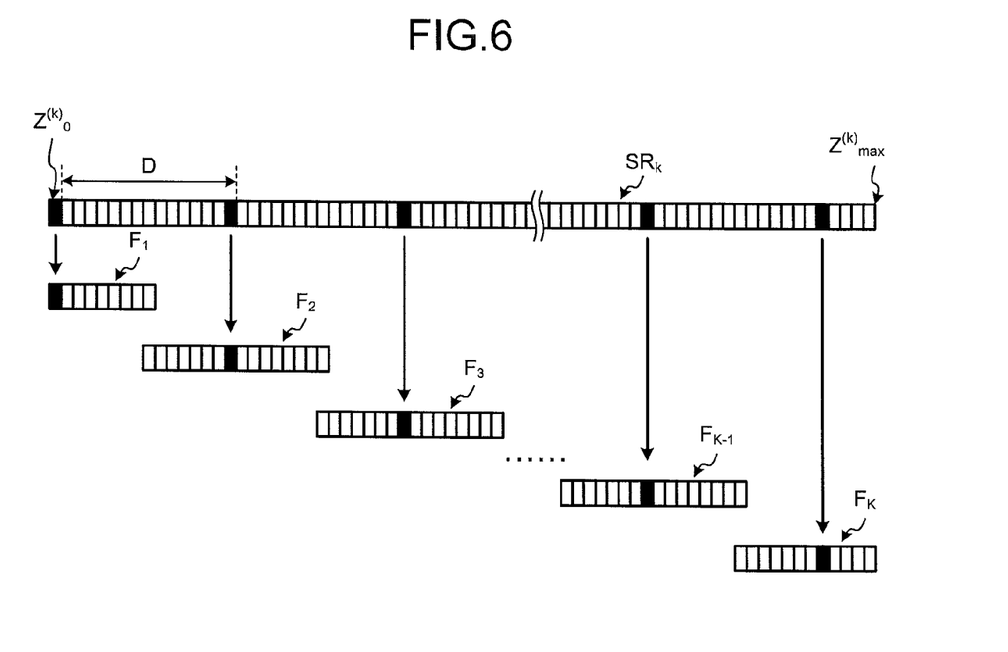
FIG. 6 is a diagram schematically illustrating a data array of a single acoustic ray to be processed by the ultrasonic observation apparatus according to the first embodiment of the present invention.

Subsequently, the FFT processing unit 42 sets an initial value $Z^{(k)}_0$ of a data position (corresponding to a reception depth) $Z^{(k)}$ a series of data group (FFT data group) acquired for FFT operation (step S22). FIG. 6 is a diagram schematically illustrating a data array of a single acoustic ray. In an acoustic ray $SR_k$ illustrated in the drawing, a rectangle in white or black means a single piece of data. The acoustic ray $SR_k$ is discretized at time intervals corresponding to a sampling frequency (e.g., 50 MHz) in A/D conversion performed by the transmitting and receiving unit 3. Although FIG. 6 illustrates a case where the first data position in the acoustic ray $SR_k$ is set to be the initial value $Z^{(k)}_0$, the position of the initial value can be set arbitrary.

Then, the FFT processing unit 42 acquires the FFT data group at the data position $Z^{(k)}$ (step S23), and applies the window function stored in the window function storage unit 82 to the acquired FFT data group (step S24). In this way, by applying the window function to the FFT data group, it is possible to avoid the FFT data group becoming discontinuous at the boundary, and to prevent generation of artifacts.

Subsequently, the FFT processing unit 42 determines whether or not the FFT data group at the data position $Z^{(k)}$ is a normal data group (step S25). Here, the FFT data group must have the number of data of a power of two. Hereinafter, the number of data of the FFT data group is assumed to be $2^n$ (n is a positive integer). The FFT data group being normal means the data position $Z^{(k)}$ is at the $2^{n-1}$ th position from the front in the FFT data group. In other words, the FFT data group being normal means that $2^{n-1}$ (=N) pieces of data are located in front of the data position $Z^{(k)}$, and $2^{n-1}$ (=M) pieces of data are located behind the data position $Z^{(k)}$. In the case illustrated in FIG. 6, both the FFT data groups $F_2$ and $F_3$ are normal, provided that n=4 (N=7, M=8) in FIG. 6.

As a result of determination at step S25, if the FFT data group at the data position $Z^{(k)}$ is normal (step S25: Yes), the FFT processing unit 42 proceeds to step S27 described below.

As a result of the determination at step S25, if the FFT data group at the data position $Z^{(k)}$ is abnormal (step S25: No), the FFT processing unit 42 generates a normal FFT data group by inserting zero data for the shortfall (step S26). The window function has been applied to the FFT data group determined as abnormal at step S25 before adding zero data. Therefore, even if zero data is inserted in the FFT data group, data discontinuity will not occur. After step S26, the FFT processing unit 42 proceeds to step S27 described below.

At step S27, the FFT processing unit 42 performs FFT operation using the FFT data group to thereby acquire a frequency spectrum which is a complex number (step S27).

Subsequently, the FFT processing unit 42 changes the data position $Z^{(k)}$ by a step width D (step S28). The step width D is assumed to be stored in advance in the storage unit 8. FIG. 6 illustrates an exemplary case where D=15. It is desirable that the step width D is equal to the data step width to be used when the image data generation unit 5 generates B mode image data. However, if it is desirable to reduce the operation amount in the FFT processing unit 42, a value larger than the data step width used by the image data generation unit 5 may be set.

Then, the FFT processing unit 42 determines whether or not the data position $Z^{(k)}$ is larger than a maximum value $Z^{(k)}_{max}$ in the acoustic ray $SR_k$ (step S29). If the data position $Z^{(k)}$ is larger than the maximum value $Z^{(k)}_{max}$ (step S29: Yes), the FFT processing unit 42 increments the counter k by one (step S30). On the other hand, if the data position $Z^{(k)}$ is the maximum value $Z^{(k)}_{max}$ or smaller (step S29: No), the FFT processing unit 42 returns to step S23. In this way, the FFT processing unit 42 performs FFT operation on the [$\{(Z^{(k)}_{max} - Z^{(k)}_0)/D\}+1$] FFT data groups, with respect to the acoustic ray $SR_k$. In this example, [X] represents a maximum integer not exceeding X.

After step S30, the FFT processing unit 42 determines whether or not the counter k is larger than a maximum value $k_{max}$ (step S31). If the counter k is larger than $k_{max}$ (step S31: Yes), the FFT processing unit 42 ends the series of FFT processing. On the other hand, if the counter k is $k_{max}$ or smaller (step S31: No), the FFT processing unit 42 returns to step S22.

It is noted that while, in this example, it is the premise that the FFT processing unit 42 performs FFT processing on the entire area where a ultrasonic signal is received, it is possible to accept an setting input of a particular area of concern by the input unit 6 beforehand and perform FFT processing in the area of concern.

Figure 7:
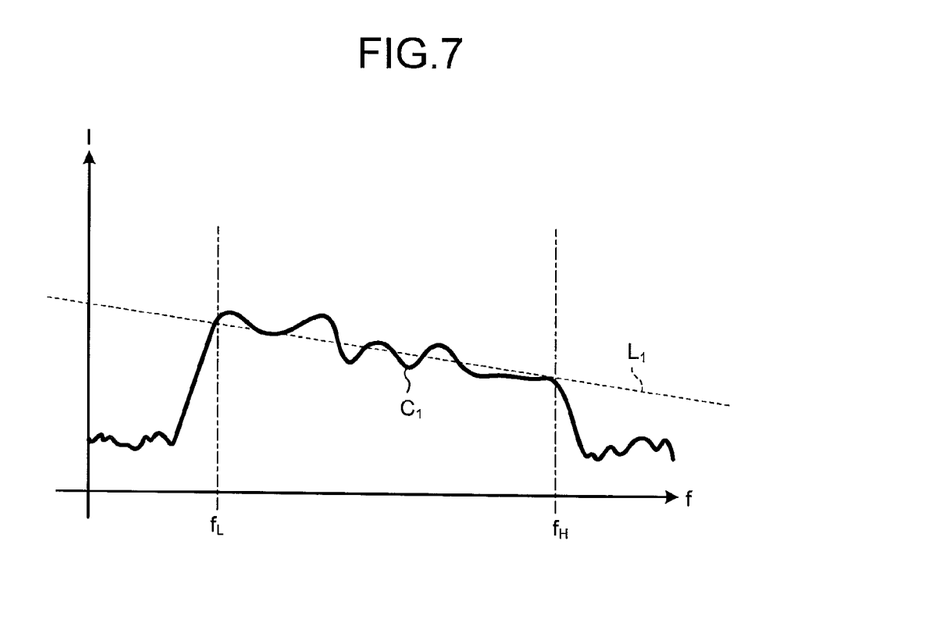
FIG. 7 is a diagram illustrating an exemplary frequency spectrum calculated by the FFT processing unit of the ultrasonic observation apparatus according to the first embodiment of the present invention.

FIG. 7 is a diagram illustrating an exemplary frequency spectrum calculated by the FFT processing unit 42. In FIG. 7, the horizontal axis f shows a frequency and the vertical axis I shows intensity. A frequency spectral curve $C_1$ illustrated in FIG. 7 gives an intensity spectrum excluding a phase component at a data position (reception depth) $Z^{(k)}$. It is noted that in the first embodiment, a curve and a straight line including a set of discrete points. This is also the same even in the embodiments described below. A frequency band is determined based on the frequency band of the ultrasonic probe 2, the frequency band of a pulse signal transmitted by the transmitting and receiving unit 3, and the like. In the case illustrated in FIG. 7, the frequency band is a band between the lower limit frequency $f_L$ and the upper limit frequency $f_H$. Specific values of the lower limit frequency $f_L$ and the upper limit frequency $f_H$ of the frequency spectrum in this case are $f_L=3$ MHz and $f_H=10$ MHz, for example. It is noted that at a point where the reception depth is larger than a given value among the points on the acoustic ray, the upper limit value of the frequency band may be set to a value smaller than the upper limit frequency $f_H$. Further, the frequency band illustrated in FIG. 7 is merely an example. Another value in the proximity of the upper limit frequency $f_H$ may be set as an upper limit value, while another value in the proximity of the lower limit frequency $f_L$ may be set as a lower limit value. The straight line $L_1$ illustrated in FIG. 7 will be described below.

Further description will be continued by returning to the flowchart of FIG. 4. Subsequent to the FFT processing at step S4 described above, the regression analysis unit 43 performs regression analysis on the frequency spectrum calculated by the FFT processing unit 42 to thereby extract a parameter of the regression expression (step S5). Specifically, the regression analysis unit 43 calculates a regression expression (linear expression) of a frequency spectrum having a frequency band $f_L < f < f_H$ by regression analysis to thereby extract slope "a". The straight line $L_1$ illustrated in FIG. 7 is a regression line obtained by performing regression analysis processing on the frequency spectral curve $C_1$ by the regression analysis unit 43 at this step S5.

Figure 8:
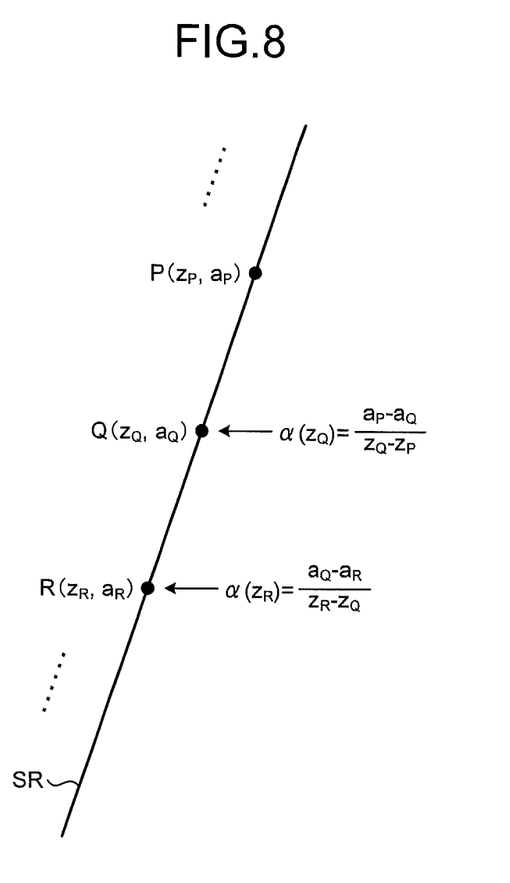
FIG. 8 is a diagram schematically illustrating attenuation correction coefficient calculation processing performed by an attenuation correction coefficient calculation unit of the ultrasonic observation apparatus according to the first embodiment of the present invention.

Then, the attenuation correction coefficient calculation unit 44 calculates the attenuation correction coefficient α according to Expression (1) described above (step S6). FIG. 8 is a diagram schematically illustrating attenuation correction coefficient calculation processing performed by the attenuation correction coefficient calculation unit 44. The acoustic ray SR illustrated in FIG. 8 shows three points P, Q, and R adjacent to each other along the direction of the reception depth on a single acoustic ray from which attenuation correction coefficients are calculated. It is assumed that the reception depths of the points P, Q, and R are $z_P$, $z_Q$, and $z_R$, respectively ($z_P < z_Q < z_R$). It is also assumed that the slopes of the approximate straight lines of the frequency spectrums at the points P, Q, and R are $a_P$, $a_Q$, and $a_R$, respectively. In this example, the attenuation correction coefficient $\alpha(z_Q)$ at the point Q is calculated by substituting the reception depth $z_Q$ and the slope $a_Q$ of itself, and the reception depth $z_P$ and the slope $a_P$ of the point P which is adjacent thereto and has a smaller reception depth than that of itself, into Expression (1) as follows:

$$\alpha(z_Q) = (a_P - a_Q)/(z_Q - z_P) \quad (3)$$

Similarly, the attenuation correction coefficient $\alpha(z_R)$ at the point R is calculated by substituting the reception depth $z_R$ and the slope $a_R$ of itself, and the reception depth $z_Q$ and the slope $a_Q$ of the point Q which is adjacent thereto and has a smaller reception depth than that of itself, into Expression (1) as follows:

$$\alpha(z_R) = (a_Q - a_R)/(z_R - z_Q) \quad (4)$$

The attenuation correction coefficients calculated by the attenuation correction coefficient calculation unit 44 in this way are stored in the attenuation correction information storage unit 83.

Figure 9:
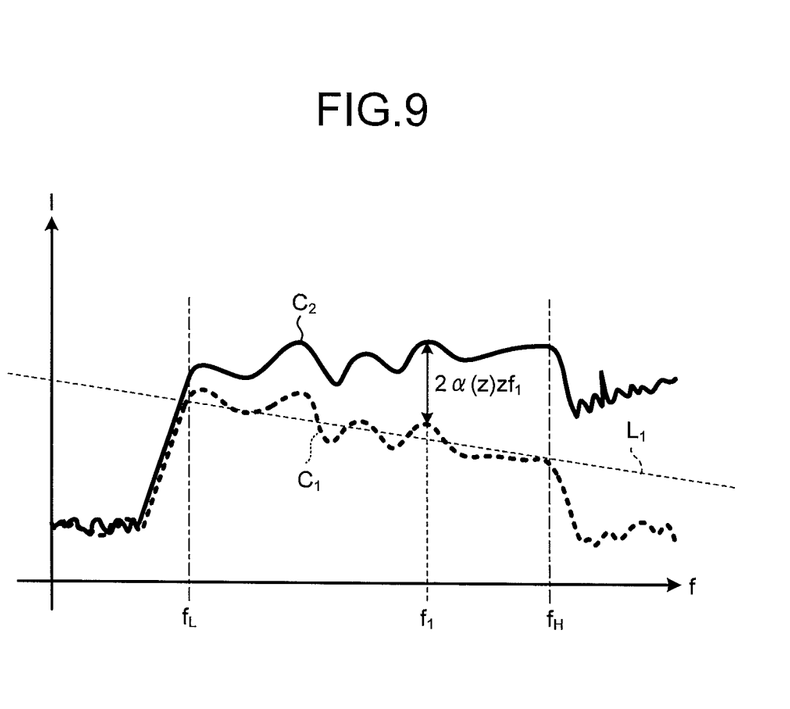
FIG. 9 is a diagram illustrating the outline of attenuation correction processing performed by an attenuation correction processing unit of the ultrasonic observation apparatus according to the first embodiment of the present invention.

Subsequently, the attenuation correction processing unit 45 performs attenuation correction processing based on the attenuation correction coefficients calculated by the attenuation correction coefficient calculation unit 44 (step S7). FIG. 9 is a diagram illustrating the outline of attenuation correction processing performed by the attenuation correction processing unit 45. The attenuation correction processing unit 45 performs attenuation correction on the frequency spectrum using Expression (3). Specifically, the intensity spectrum I(f, z) is corrected according to the following Expression (5):

$$I'(f,z) = I(f,z) + 2\alpha(z)zf \quad (5)$$

Thereby, a frequency spectral curve $C_2$ after the attenuation correction is obtained.

It is noted that when calculating the attenuation correction coefficient at the point Q in FIG. 8, the data positions and the slopes of the point Q and the point R may be used. As shown above, when calculating an attenuation correction coefficient of a point, the way of selecting a point other than oneself is not limited to those described above.

Then, the IFFT processing unit 46 performs IFFT processing on the frequency spectrum after the attenuation correction (step S8). Specifically, the IFFT processing unit 46 performs IFFT processing on a complex number which is obtained by adding the phase component of the frequency spectrum before correction to the intensity spectrum I'(f,z) of Expression (5). Thereby, an ultrasonic signal of a time domain, on which attenuation correction dependent on the frequency has been performed, is obtained.

Subsequently, the image data generation unit 5 generates image data based on the ultrasonic signal of a frequency domain on which attenuation correction has been performed by the computing unit 4 (step S9).

The display unit 7 displays an image corresponding to the image data generated by the image data generation unit 5 (step S10).

According to the first embodiment of the present invention described above, attenuation correction processing on the signal, on which FFT processing was performed, is performed using the attenuation correction coefficients calculated based on the first-order coefficients in the regression expressions of two or more points having different reception depths. Subsequently, ultrasonic image data is generated based on the time domain signal obtained by performing IFFT processing. Thereby, it is possible to perform appropriate attenuation correction in real time based on the measurement result.

Further, according to the first embodiment, by correcting attenuation dependent on the frequency, it is possible to display an ultrasonic image having good spatial resolution even in an area distant from the ultrasonic probe.

It is noted that while, in the first embodiment, attenuation correction coefficients are calculated using two points on a single acoustic ray, more generally, attenuation correction coefficients may be calculated using a plurality of points on a single acoustic ray. For example, in the case of using three points, there are three ways of combining two points among the three points. In that case, it is only necessary that the attenuation correction coefficient calculation unit 44 first calculates an attenuation correction coefficient between adjacent two points based on Expression (1), and then calculates an average value of the two attenuation correction coefficients calculated, as a final attenuation correction coefficient. Further, in the case of using three points, it is possible that the attenuation correction coefficient calculation unit 44 calculates attenuation correction coefficients with respect to all of the combinations of two points which can be obtained from the three points, and calculates an average value as a final attenuation correction coefficient.

Second Embodiment

Figure 10:
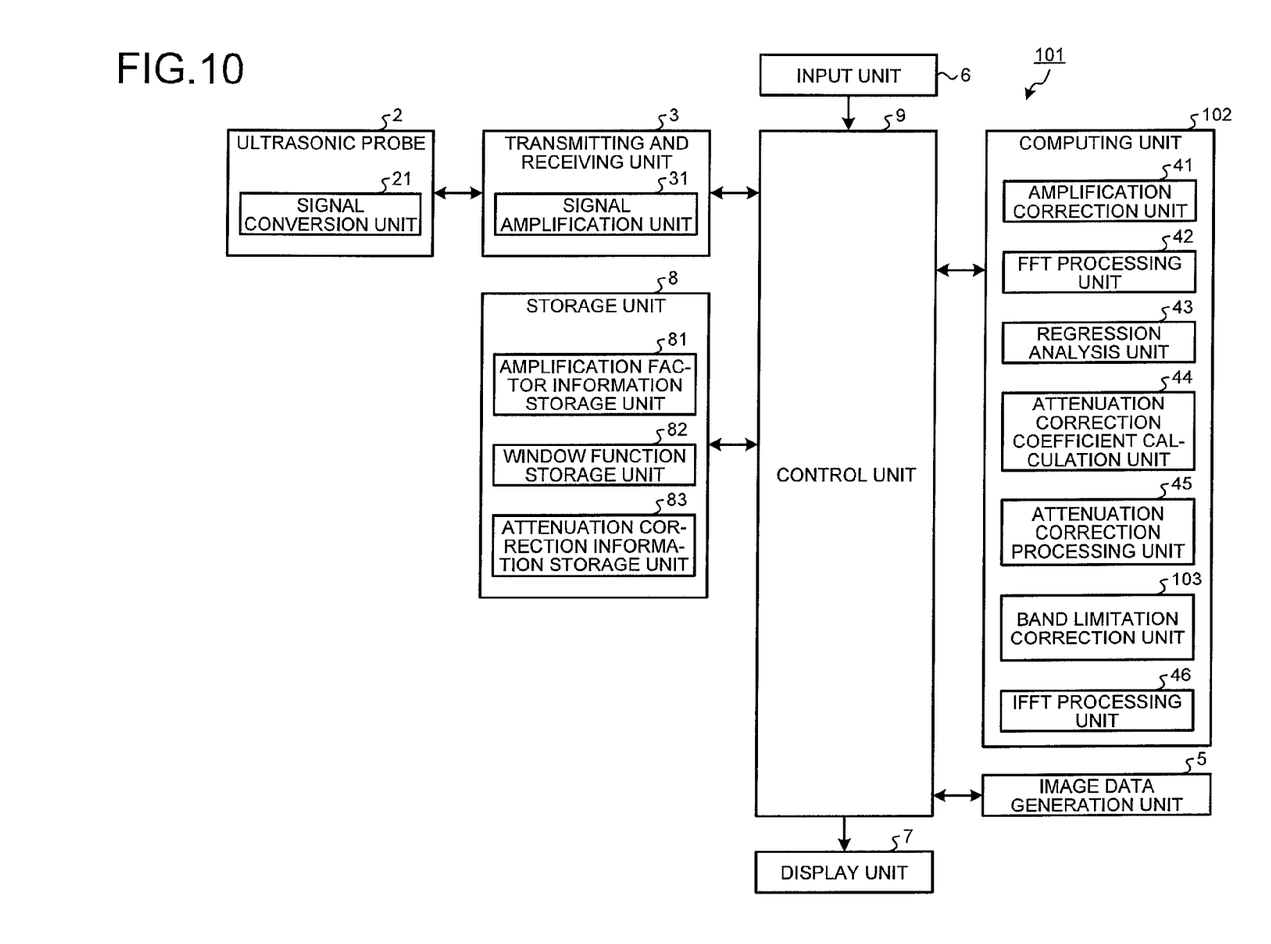
FIG. 10 is a block diagram illustrating a configuration of an ultrasonic observation apparatus according to a second embodiment of the present invention.

FIG. 10 is a block diagram illustrating a configuration of an ultrasonic observation apparatus according to a second embodiment of the present invention. An ultrasonic observation apparatus 101 illustrated in the drawing is different in the configuration of a computing unit 102, compared with the ultrasonic observation apparatus 1. Therefore, elements having similar functions as those of the elements of the ultrasonic observation apparatus 1 are denoted by the same reference signs.

The computing unit 102 includes a band limitation correction unit 103, in addition to the configuration included in the computing unit 4 (the amplification correction unit 41, the FFT processing unit 42, the regression analysis unit 43, the attenuation correction coefficient calculation unit 44, the attenuation correction processing unit 45, and the IFFT processing unit 46) of the ultrasonic observation apparatus 1.

The band limitation correction unit 103 performs correction to limit the frequency band to thereby reduce contribution of frequency components outside the given frequency band, with respect to the frequency spectrum on which correction has be performed by the attenuation correction processing unit 45. As such a correction, the band limitation correction unit 103 performs processing to replace unnecessary spectral intensity with zero, in a frequency component outside the given frequency band, for example. This processing can be performed by applying a specified window function to the frequency spectrum, for example.

According to the second embodiment of the present invention described above, in addition to an advantageous effect similar to that of the first embodiment described above, it is possible to prevent noise of a high-frequency component from being emphasized excessively due to attenuation correction.

It is noted that in the second embodiment, the attenuation may be performed by multiplying a specified weight, instead of replacing unnecessary spectral intensity with zero.

Further, in the second embodiment, the band limitation correction unit 103 may attenuate unnecessary spectral intensity with respect to the ultrasonic signal of a time domain obtained by performing IFFT processing by the IFFT processing unit 46.

Other Embodiments

Figure 11:
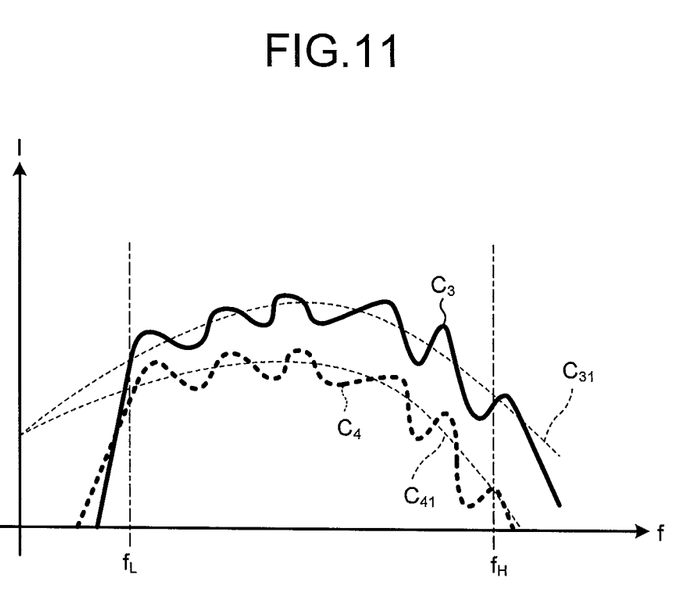
FIG. 11 is a frequency spectral curve and an approximate curve thereof calculated by an ultrasonic observation apparatus according to another embodiment of the present invention.

While modes for carrying out the present invention have been described, the present invention is not limited to the two embodiments described above. FIG. 11 is a diagram illustrating a frequency spectral curve calculated by an ultrasonic observation apparatus according to another embodiment of the present invention, and a regression curve obtained by performing regression analysis on the frequency spectral curve. In FIG. 11, a curve $C_{31}$ is a regression curve of a frequency spectral curve $C_3$ (assumed to have a reception depth $z_3$), and a curve $C_{41}$ is a regression curve of a frequency spectral curve $C_4$ (assumed to have a reception depth $z_4$ ($>z_3$)).

On the assumption that attenuation along with propagation of an ultrasonic wave is proportional to the reception depth and the frequency, respectively, in a difference between an expression of the frequency spectral curve $C_3$, that is, $I_3(f)=c_{30}+c_{31}f+c_{32}f^2+\ldots$ and an expression of the frequency spectral curve $C_4$, that is, $I_4(f)=c_{40}+c_{41}f+c_{42}f^2+\ldots$, a first-order term becomes dominant.

$$I_3(f)-I_4(f) \sim (c_{31}-c_{41})f \qquad (6)$$

Accordingly, an attenuation correction coefficient $\alpha$ between the reception depth $z_3$ and the reception depth $z_4$ can be defined as follows:

$$\alpha=(c_{31}-c_{41})/(z_4-z_3) \qquad (7)$$

In this way, even in the case where the frequency spectrum cannot be approximated by a linear expression, it is possible to calculate an attenuation correction coefficient accurately and easily by performing regression analysis using a more general polynomial.

Further, in general, as for an image generated based on amplitude information, it is possible to obtain an advantageous effect similar to that described above by performing frequency-dependent attenuation correction. Such an image includes an A mode image, a C mode image, and a three-dimensional display image.

Further, tissue characterization of a body tissue may be determined using an attenuation correction coefficient calculated by the attenuation correction coefficient calculation unit. This is because, in the case where the observation target is a body tissue, it is known that an attenuation correction coefficient of an ultrasonic wave has a relation with the tissue characterization of the body tissue.

As obvious from the above description, the present invention may include various embodiments within the scope not deviating from the technical concept described in the claims.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic observation apparatus comprising:
a transmitting and receiving unit configured to transmit an ultrasonic signal, which is a time domain signal, to a specimen, and receive the ultrasonic signal reflected from the specimen;
a first conversion unit configured to convert the ultrasonic signal received by the transmitting and receiving unit into a frequency domain signal;

a regression analysis unit configured to calculate a regression expression for the frequency domain signal converted by the first conversion unit;

an attenuation correction coefficient calculation unit configured to calculate an attenuation correction coefficient which is obtained by dividing a difference between first-order coefficients in the regression expressions at two points having different reception depths by a difference between the reception depths at the two points;

an attenuation correction processing unit configured to perform attenuation correction processing on the frequency domain signal based on the attenuation correction coefficient calculated by the attenuation correction coefficient calculation unit;

a second conversion unit configured to convert the frequency domain signal, on which the attenuation correction processing has been performed by the attenuation correction processing unit, into a second time domain signal; and an image data generation unit configured to generate B mode image data based on the second time domain signal.

2. The ultrasonic observation apparatus according to claim 1, wherein the attenuation correction processing unit is configured to perform the attenuation correction processing on the frequency domain signal of a larger one of the reception depths at the two points used for calculating the attenuation correction coefficient, by applying the attenuation correction coefficient calculated based on the reception depths at the two points.

3. The ultrasonic observation apparatus according to claim 1, further comprising a band limitation correction unit configured to perform correction to limit a frequency band to a given frequency band to thereby reduce contribution of a frequency component outside the given frequency band, after correction by the attenuation correction processing unit and before conversion by the second conversion unit or after conversion by the second conversion unit.

4. The ultrasonic observation apparatus according to claim 1, wherein the image data generation unit is configured to generate the B mode image data based on amplitude information of the second time domain signal.

5. An operation method of an ultrasonic observation apparatus that transmits an ultrasonic signal, which is a time domain signal, to a specimen and receives the ultrasonic signal reflected from the specimen, the method comprising:

converting the received ultrasonic signal into a frequency domain signal by a first conversion unit;

calculating a regression expression for the frequency domain signal by a regression analysis unit;

calculating an attenuation correction coefficient by an attenuation correction coefficient calculation unit, the attenuation correction coefficient being obtained by dividing a difference between first-order coefficients in the regression expressions at two points having different reception depths by a difference between the reception depths at the two points;

performing attenuation correction processing on the frequency domain signal based on the attenuation correction coefficient, using an attenuation correction processing unit;

converting the frequency domain signal, on which the attenuation correction processing has been performed, into a second time domain signal, using a second conversion unit; and generating B mode image data based on the second time domain signal, using an image data generation unit.

6. A non-transitory computer readable recording medium with an executable program stored thereon, the program instructing a processor to perform:

converting the received ultrasonic signal into a frequency domain signal by a first conversion unit;

calculating a regression expression for the frequency domain signal by a regression analysis unit;

calculating an attenuation correction coefficient by an attenuation correction coefficient calculation unit, the attenuation correction coefficient being obtained by dividing a difference between first-order coefficients in the regression expressions at two points having different reception depths by a difference between the reception depths at the two points;

performing attenuation correction processing on the frequency domain signal based on the attenuation correction coefficient, using an attenuation correction processing unit;

converting the frequency domain signal, on which the attenuation correction processing has been performed, into a second time domain signal, using a second conversion unit; and generating B mode image data based on the second time domain signal, using an image data generation unit.

* * * * *